United States Patent [19]

Boland et al.

[11] Patent Number: 4,747,846
[45] Date of Patent: May 31, 1988

[54] STRETCHABLE DISPOSABLE ABSORBENT UNDERGARMENT

[75] Inventors: Leona G. Boland, Neenah; Georgia L. Zehner, Larsen; Robert A. Stevens, Appleton, all of Wis.

[73] Assignee: Kimberly-Clark Corporation, Neenah, Wis.

[21] Appl. No.: 34,818

[22] Filed: Apr. 3, 1987

[51] Int. Cl.⁴ .............................................. A61F 13/16
[52] U.S. Cl. ................................. 604/38.A; 604/396
[58] Field of Search ................. 604/385.1, 385.2, 394, 604/395, 396, 378

[56] References Cited

U.S. PATENT DOCUMENTS

| | | |
|---|---|---|
| 2,141,105 | 12/1938 | Eller et al. . |
| 3,196,874 | 7/1965 | Hrubecky . |
| 3,370,590 | 2/1968 | Hokanson et al. . |
| 3,644,157 | 2/1972 | Draper ................................ 156/160 |
| 3,658,064 | 4/1972 | Pociluyko . |
| 4,050,462 | 9/1977 | Woon et al. . |
| 4,166,464 | 9/1979 | Korpman . |
| 4,324,245 | 4/1982 | Mesek et al. . |
| 4,355,425 | 10/1982 | Jones et al. ............................. 2/402 |
| 4,397,646 | 8/1983 | Daniels et al. ...................... 604/381 |
| 4,425,128 | 1/1984 | Motomura ......................... 604/381 |
| 4,496,360 | 1/1985 | Joffe et al. ........................... 604/397 |
| 4,597,760 | 7/1986 | Buell ................................... 604/397 |
| 4,597,761 | 7/1986 | Buell ................................... 604/397 |
| 4,610,680 | 9/1986 | LaFleur .............................. 604/385 |
| 4,610,681 | 9/1986 | Strohbeen et al. .................. 604/396 |
| 4,619,649 | 10/1986 | Roberts ............................... 604/396 |

FOREIGN PATENT DOCUMENTS

0048011 3/1982 European Pat. Off. .

*Primary Examiner*—John D. Yasko
*Attorney, Agent, or Firm*—John L. Chiatalas

[57] ABSTRACT

An anatomically form-fitting, generally self-adjusting disposable absorbent slip-on undergarment that may be easily raised and lowered by the wearer during use, e.g., a training pant or incontinence pad. The garment comprising a breathable elastomeric nonwoven laminar outer cover having an absorbent insert structure attached and integrated thereto while allowing substantially unrestricted functional stretchability of the outer cover. The outer cover has closed side panels connecting the front and rear panels and the leg and waist openings thereof, including manually separable side seams having breakable ultrasonic bonds for removing the garment from the wearer upon soiling, without removal of the wearer's outer clothing.

11 Claims, 5 Drawing Sheets

STRETCHABLE DISPOSABLE ABSORBENT UNDERGARMENT

TECHNICAL FIELD

The present invention relates, generally, to the field of disposable garments utilized for the absorption and containment of urine and other bodily exudates. More particularly, the present invention relates to pull-on undergarments, such as disposable training pants, incontinent garments and the like.

BACKGROUND OF THE INVENTION

Disposable garments are generally well known in the art and have become an important and an essentially indispensable sanitary protection item, most particularly in the field of infant and child care where disposable diapers provide for the absorption and containment of urine and other bodily exudates. Present commercially available disposable diapers are generally unitary, preshaped and prefolded, and comprised of a porous facing layer and a fluid impervious backing sheet with an absorbent material disposed therebetween. These presently available disposable diapers have met a particular need and have become ever increasingly popular. However, even though the present available disposable diapers have achieved a certain degree of efficiency and effectiveness, several draw-backs remain that have been identified by mothers of infants wearing the diapers. These mothers have strongly voiced their desire to be able to obtain disposable diapers that are aesthetically neat and attractive when on their infant or child. The aesthetically neat criteria have been identified as including a trim, slim fit, and a neat fitting waist and legs that do not allow leakage of urine or feces. It has also been found that mothers do not want their children looking rumpled, bulky or messy. In addition, these mothers have expressed the desire to either have a disposable diaper that fits more sizes of babies or to have disposable diapers provided in more sizes. Another draw-back identified by these mothers has been the problem associated with skin irritation caused by urine, feces or moisture trapped next to the skin. They have again been very vocal in their desire to obtain disposable diapers that avoid or solve this problem.

The typical disposable diaper has a three-layer composite structure comprising a liquid permeable bodyside inner liner, a liquid impermeable outer cover and an absorbent batt sandwiched between the liner and the cover. Materials now in general use for the three principal elements of a disposable diaper include various types of nonwoven fabrics for the bodyside liner, a thin thermoplastic film for the outer cover and cellulosic fluff for the absorbent batt.

Disposable diapers of the type presently on the market are flat open-sided garments that are intended to be fit around an infant by a parent while the infant is lying down. The rear panel of the diaper is placed underneath the infant, and the front panel drawn between the infant's legs, after which the sides are overlapped and held together by pressure-sensitive adhesive tape. A diaper is meant for use when the child is young and dependent upon a parent for this essential purpose. Examples of present disposable diapers are taught in U.S. Pat. No. 4,324,245 to Mesek, et al., U.S. Pat. No. 3,196,874 to Hrubecky, and U.S. Pat. No. 4,050,462 to Woon, et al.

Prior art diaper constructions disclosed in the references listed below have sought to provide waste containment with a reusable diaper holder receiving an absorbent structure:
1. U.S. Pat. No. 3,658,064 to Pociluyko and U.S. Pat. No. 3,370,590 to Hokanson, et al.;
2. U.S. Pat. No. 4,425,128 to Motomura;
3. U.S. Pat. No. 2,141,105;
4. U.S. Pat. No. 4,397,646 to Daniels, et al.;
5. U.S. Pat. Nos. 4,597,761, 4,496,360 and 4,597,760.

Other diapers, e.g., U.S. Pat. No. 4,166,464 to Korpman, have utilized elastic fluid impermeable backing films laminated to an absorbent layer in an attempt to provide enhanced conformability to the body surface.

U.S. Pat. Nos. 4,355,425 to Jones, et al. and 3,644,157 to Draper disclose disposable stretchable nonwoven panties unsuitable for absorbing and containing body wastes.

Even where prior art designs have attempted to use impermeable elastic film barriers, there has been inadequate recognition of the functional problems associated with an elastic outer cover. Further, costly woven diaper holders or overpants, designed to be waterproof and reusable, do not offer a truly disposable capability.

U.S. Pat. No. 4,610,681 to Strohbeen, et al., assigned to the instant assignee, the entire disclosure of which is incorporated by reference herein and relied upon, discloses a disposable underpant, such as a child's pull-on training pant, having a multi-layer web and sealed with exterior side seams. The training pant includes elasticized leg and waist openings but otherwise has nonelastomeric components. The side seams join together closed side panels of the pant, allowing the child to raise and lower the pant unassisted during toilet training. Should the pant "accidentally" become soiled, the side seams are manually separable to allow removal of the pant without requiring removal of any outer clothing from the child. The outer cover of the pant comprises a nonwoven material with a simulated cloth feel intended to further enhance the transition from infant diapers to reusable cloth underpants which are worn after the toilet training period.

U.S. Pat. Nos. 4,610,680 and 4,619,649 both disclose a training pant wherein a tear strand allows the pant to be separated for removal from the child when soiled. Likewise European Patent Application No. 0,048,011 A1, published Mar. 24, 1982, discloses a tear string allowing the panty to be separated for removal upon soiling.

Although the above-mentioned prior art diapers and training pants are provided with elasticized leg and/or waist openings, there is still a tendency for the garment to blouse outwardly from the body at the hip and lower abdominal regions. Thus, there remains a need for an anatomically form-fitting, generally self-adjusting training pant or other disposable underpant that may be worn and used unassisted, either by a child in toilet training or by an incontinent adult, and then easily removed when soiled without a mess.

SUMMARY OF THE INVENTION AND ADVANTAGES

According to the instant invention, there is provided an anatomically form-fitting, generally self-adjusting three-dimensional disposable absorbent undergarment comprising a breathable elastomeric nonwoven outer cover wherein an elastic nonwoven web is joined to one or more gatherable nonwoven webs, including a pair of leg openings, front and rear waist sections together defining a waist opening, a crotch section situated between the leg openings, opposing front and rear panels separated by the crotch section and a pair of side panels extending between and interconnecting the leg and waist openings and the front and rear panels, respectively. An absorbent insert structure is substantially superposable on the front and rear panels and the crotch section, including a liquid impermeable barrier and a liquid permeable bodyside liner with an absorbent core disposed therebetween. Attachment means are provided for attaching and integrating the absorbent insert into the outer cover while allowing substantially unrestricted functional stretchability thereof. Nonrefastenable side seams extend between and interconnect the leg and waist openings of each of the side panels, including manually tearable stress release means for opening and separating the side seams and removing the garment from the wearer when the same becomes soiled.

In a preferred embodiment, the insert is attached to the outer cover at selected waist attachment zones, defining one or more free-span zones underlying the absorbent insert wherein the functional stretchability of the outer cover in the free-span zone is substantially unrestricted. Further, the outer cover may be resiliently stretchable in an essentially cross-body direction from about 20% to about 200% and have a nonrestrictive free-span zone effectively extending at least the entire longitudinal length of the rear panel.

In another preferred embodiment, the absorbent structure may be integrated to the outer cover while the outer cover is in a stretched condition.

An advantage of the instant invention is a disposable absorbent garment having a form-fitting, generally self-adjusting fit due to an elastomeric outer cover having an integrated absorbent structure which does not inhibit the functional stretch properties of the outer cover.

Another advantage of the instant invention is that the absorbent structure is held in registration with the body for absorbing and containing wastes without sagging or shifting out of place, reducing leakage from the diaper.

Another advantage of the instant invention is a pull-on absorbent garment that may be used unassisted by a child during toilet training or by an incontinent adult and then easily removed upon soiling without also removing the outer clothing.

A further advantage of the instant invention is the enhanced cloth-like comfort and feel of the garment while presenting a smooth pleasing undergarment-like appearance when worn.

DETAILED DESCRIPTION OF THE PREFERRED EMBODIMENTS

Figure 1:
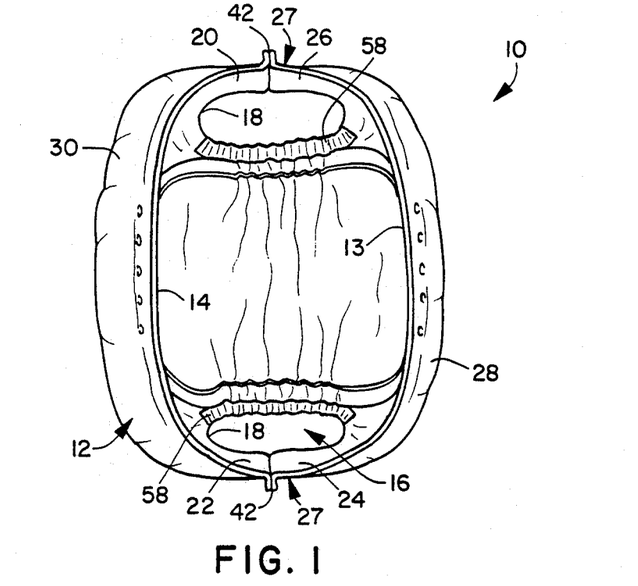
FIG. 1 is an internal perspective view of the invention.

Referring to FIG. 1, according to the instant invention, there is provided an anatomically form-fitting, generally self-adjusting disposable absorbent undergarment, generally shown at 10, such as a disposable training pant or incontinent garment, comprising an elastomeric outer cover, generally indicated at 12, including opposed front 13 and rear 14 waist sections together defining a waist opening. A crotch section, generally indicated at 16, is situated between a pair of leg openings 18 at outermost portions of said crotch section 16. Ear portions 20, 22, 24, 26 are delimited generally between the opposed waist sections 13, 14 and each of the marginal leg openings 18, respectively, with longitudinally opposed pairs of said ears 20, 26 and 22, 24 being engageable with one another about the body of a wearer, defining a pair of side panels, generally indicated at 27. Also, the outer cover 12 preferably has a generally hourglass profile with the leg openings 18 cut out from the crotch section 16 thereof, defining a front panel 28 having a laterally opposed front pair of the ear portions 24, 26 in conjunction therewith and a rear panel 30 having another laterally opposed rear pair of the ear portions 20, 22 in conjunction therewith. The front 28 and rear 30 panels are separated from one another by the crotch section 16 which is narrowed due to the converging leg cut-out openings 18.

Figures 6, 6A:
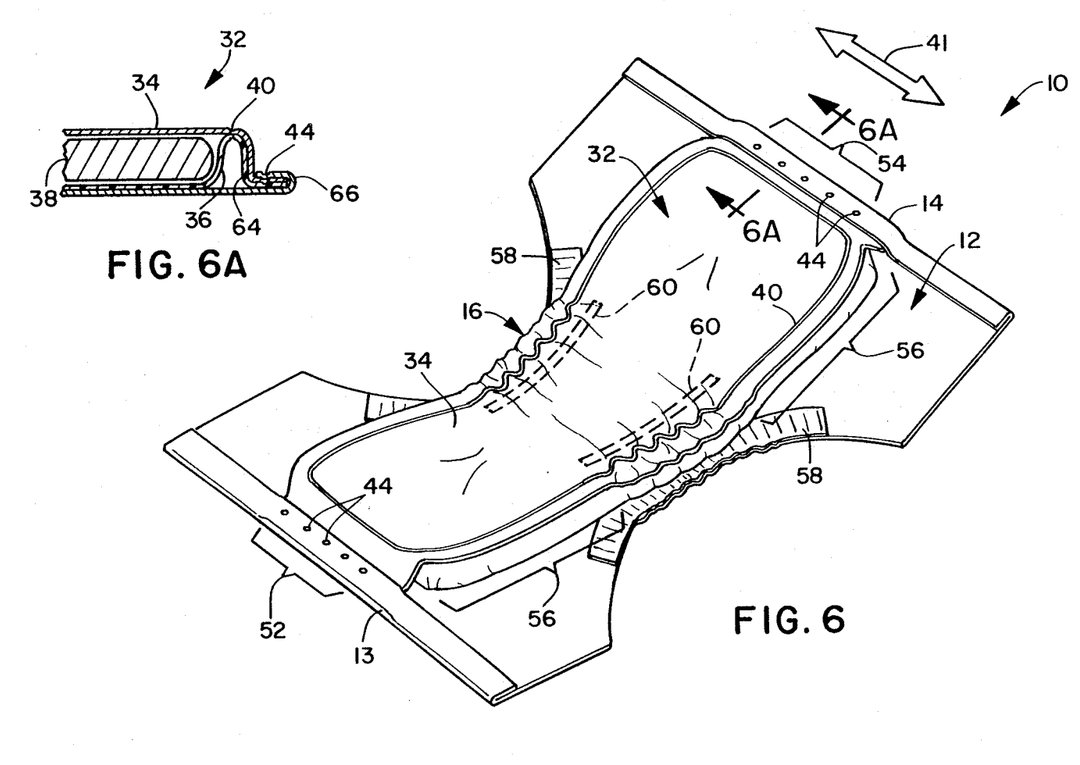
FIG. 6 is an internal view of the invention shown prior to closure of the side seams thereof.
FIG. 6A is a sectional view of cross-section 6A—6A of FIG. 6.
Figure 7:
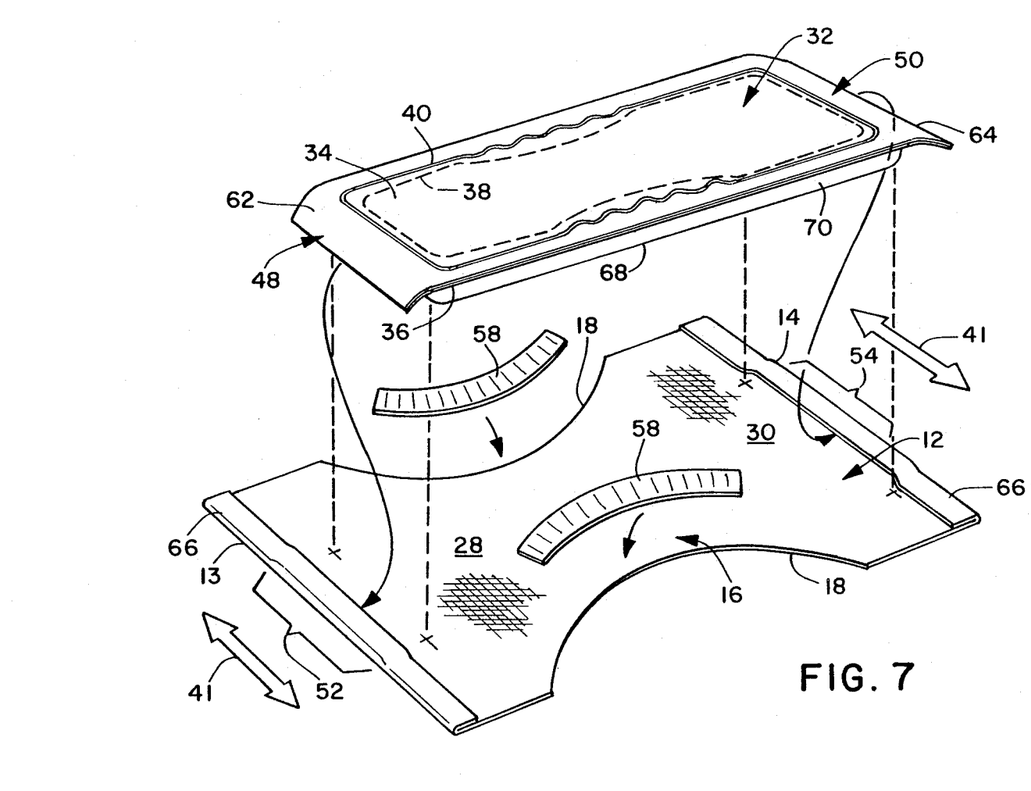
FIG. 7 is an exploded perspective view of the invention showing integration of the absorbent insert structure into the outer cover.
Figure 8:
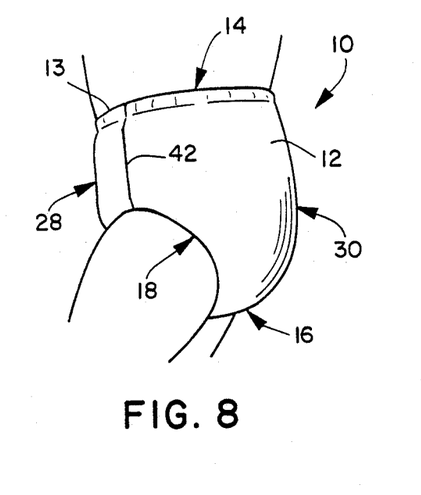
FIG. 8 is a side view of the disposable absorbent undergarment of the present invention shown secured around a baby.
Figure 9:
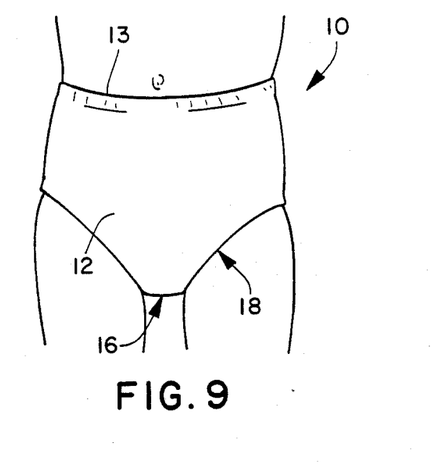
FIG. 9 is a front view of the disposable absorbent undergarment of the present invention shown secured around a baby.
Figure 10:
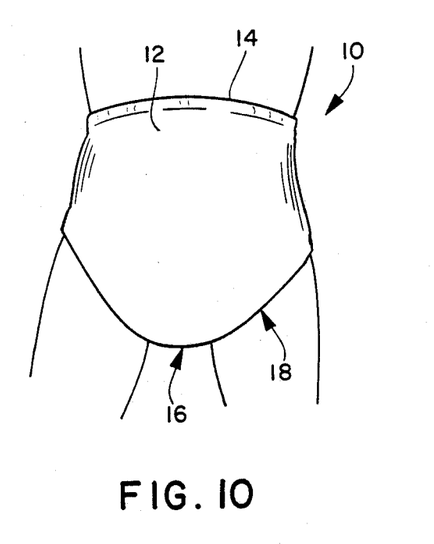
FIG. 10 is a back view of the disposable absorbent undergarment of the present invention shown secured around a baby.

With reference to FIG. 7, there is depicted an absorbent structure, generally indicated at 32, substantially superposable on the front 28 and rear 30 panels and the crotch section 16 of the outer cover 12 for absorbing and containing bodily exudates. The absorbent structure 32 includes: a liquid-permeable bodyside liner 34, for example, a commercially available pattern-bonded, spunbonded polypropylene web that may have a basis weight of from about 0.2 to 0.8 oz./yd$^2$.; a liquid-impervious barrier 36, for example, a commercially available plastic film of polypropylene or the like; and an absorbent core 38 disposed therebetween. As shown in FIGS. 6 and 7, the absorbent structure 32 is in the form of a separate insert, typically of substantially non-stretchable materials, attached and integrated into the resiliently stretchable outer cover 12 using, e.g., autogenous bonds of the type generated thermally or ultrasonically, allowing substantially unrestricted functional stretchability of the outer cover. A preferably continuous ultrasonic or thermal perimeter bond 40 sealingly secures the absorbent structure 32 together to prevent leakage therefrom by bonding the liner 34 and barrier 36 peripherally to one another about the absorbent core 38 which is disposed therebetween. It is important that the materials of the barrier 36 and liner 34 be compatible with one another and with the material of the outer cover for autogenous bonding. Accordingly, polypropylene and other polyolefins have been found to be suitable materials for use in the liner, barrier and outer cover.

The outer cover 12 generally comprises an air-permeable, i.e., "breathable", elastomeric nonwoven laminar fabric wherein an elastic nonwoven web is joined to one or more gatherable nonwoven webs. Preferably, the laminate is resiliently stretchable from about 20 to about 200 percent in an essentially cross-body direction 41. The longitudinally opposed ears 20, 26; 22, 24, which are engageable with one another to form the closed side panels 27, are joined together by a pair of side seams 42 substantially from the waist to the leg openings. The full-length closures of the side panels 27 can be reinforced to further provide dimensional integrity to the resiliently stretchable garment during various and even extreme bodily movements and positions of the wearer. Since the undergarment is form-fitting and self-adjusting, it does not gap or collapse at the hip and waist regions Preferably, the waist sections 13, 14 of the outer cover 12 have the insert 32 attached and integrated thereinto by attachment means according to the present invention as will be set forth more fully below.

With respect to the attachment means of the present invention as shown in FIGS. 6 and 6A, it is important to minimize the number of bonds and total bond area used in integrating the relatively unstretchable absorbent insert to the stretchable outer cover or, where forming hems, the number of bonds used to bond the outer cover to itself. The Applicants have discovered that the number of bonds correspondingly affects the stretch elongation in the elastomeric component that is bonded. Not only does a lesser number of bonds result in less stretch loss, but the greater the spacing apart of bond points, the less stretch elongation is affected. Accordingly, bonding patterns should be selected that significantly reduce the amount of stretch lost by means of the density and spacing of the bond points. Specifically, the lower the number and density of the bonds 44 for attaching and integrating the insert 32 along the waist sections 13, 14, the less stretch is inhibited in said waist sections. For example, if the waist section is stretchable in a cross-body direction and the insert is attached thereto at two points lying on a line extending also in said cross-body direction, then the stretchability of the outer cover waist section along that line is restricted between those two points of attachment by the least stretchable element present between those points, usually the liner or barrier of the insert. Similarly, the insert may also be attached and integrated at the crotch section.

Therefore, the garment of the present invention includes attachment means for attaching and integrating an absorbent insert structure, used for absorbing and containing body wastes, into a relatively stretchable elastomeric outer cover used for positioning the insert in bodily registration, while allowing substantially unrestricted functional stretchability thereof, maintaining the total garment anatomically form-fitting and generally self-adjusting. These objectives have heretofore been augmented by utilizing a full-length, fixed-position fastening system in combination with the above components, such as that taught in copending U.S. patent application Ser. No. 902,828, the entire disclosure of which is hereby incorporated by reference and relied upon.

The instant undergarment 10 is generally constructed and assembled as shown by FIGS. 6–7. The bonds 44 attach and integrate the opposed longitudinal ends 48, 50 of the absorbent insert 32 to said outer cover 12 at selected front 52 and rear 54 waist attachment zones along said front 13 and rear 14 waist sections, respectively, defining one or more free-span zones 56 underlying said insert 32 wherein the functional stretchability of said outer cover in said free-span zone 56 is substantially unrestricted. It will be understood that where the insert 32 is integrated only at the waist attachment zones 52, 54, i.e., not at the crotch section 16, the free-span zone underlies the entire longitudinal length of the absorbent insert 32. Significantly, the free-span zone 56 also includes those portions of the waist sections 13, 14 not included in the waist attachment zones 52, 54. It will also be understood that the insert 32 may be adequately held by the outer cover 12 in registration with the body of the wearer without additional bonding in the free-span zone 56 to the front 28 or rear 30 panels or the crotch section 16. Moreover, stretch restriction of the outer cover, even in the waist attachment zones 52, 54 can be ameliorated by the instant invention as further set forth herein.

Although the free-span zones 56 can be provided in either of the front 28 and rear 30 panels, it is the stretch properties of the rear panel 30, which are more important. It should be noted, that cross-body stretch in the crotch section 16 of the outer cover 12 during use is minimally required so that bonding of the insert at or near the leg openings 18 of the crotch section 16 does not significantly affect the overall cross-body stretch properties of the outer cover. The breathable outer cover 12, among other functions, holds the insert 32 in proper bodily registration and, unlike the prior art, is not itself required to provide a liquid waste containment barrier.

Referring to FIG. 7, the absorbent insert 32 may further comprise at least one but preferably a pair of front 62 and rear 64 waist attachment flaps respectively situated at the opposed longitudinal ends 48, 50 of the insert 32. The flaps 62, 64 extend longitudinally from and contiguous with the liner 34 beyond the terminal ends of the absorbent composite 38, the flaps being bonded or otherwise attached to said front 13 and rear 14 waist sections, respectively, in said waist attachment zones 52, 54. The front 13 and rear 14 waist sections preferably have finished waist hems 66 along the waist opening wherein the waist attachment flaps 62, 64 are entrapped and bonded. The waist hems 66 comprise inwardly folded-over edges of outermost portions of said waist sections 13, 14.

According to the invention, therefore, the waist attachment flaps 62, 64 (FIGS. 6A and 7) may comprise coextensions of the barrier 36 and liner 34 or may comprise expansions of either the barrier 36 or liner 34 alone. The flaps 62, 64 typically comprise nonwoven and/or plastic film materials that are not inherently stretchable relative to the outer cover; however, the flaps 62, 64 themselves need not be contiguous with the liner or barrier material.

Referring again to FIGS. 6 and 7, additional elastication or bonding between other areas of the outer cover 12 and absorbent insert 32 may be provided for further contour and fit. Specifically, supplemental leg elastics 58 may be applied to outermost portions of the crotch section 16 around the inner curvature of the leg openings 18 to gather the garment 10 about the thighs of the wearer. Crotch elastics 60 may be applied to the liner 34 to cause the insert to more closely conform to the contours of the wearer's perineal region.

The leg elastics 58 preferably comprise a breathable elastomeric nonwoven laminate of the type described in copending U.S. patent application Ser. No. 947,949, the entire disclosure of which is hereby incorporated by reference and relied upon. The leg elastic members 58 function cooperably with the stretchable outer cover for gathering the leg openings 18 about the wearer and can be applied in varying tensions relative thereto by adhesive, autogenous or pressure bonding. Leg hems (not shown) may alternatively be formed at the curved leg openings 18 in addition to the waist sections 13, 14, resulting in increased tension due to the increased thickness of the elastomeric material of the outer cover at the folded over hem. However, additional elastic members (not shown) of, e.g., FULLASTIC®, a trademarked extruded elastomeric film material sold by H. B. Fuller Company of Minneapolis, Minn., can be entrapped within the waist hems 66 and any leg hems (not shown) to provide elastic gathering. Although the waist opening has heretofore been discussed in conjunction with waist hems 66 and optional waist elastics entrapped therein, a nonwoven elastomeric laminar material of the type described for the leg elastics 58 could be applied as a border strip (not shown) along the waist opening.

As can be seen in FIG. 7, the barrier 36 closely surrounds the bottom 68, and sides 70 of the absorbent core 38 (shown in phantom) with the liner 34 extending across and contacting the top surface of the absorbent core 38, imparting a generally rectangular boat-shaped configuration to the insert 32. The bottom 68 of the barrier 36 may include one or more relaxed localized areas adjacent the bottom 68 of the absorbent core 38 to accommodate swelling of the core during use with, for example, a hydrogel material. The perimeter bond 40 between the liner 34 and barrier 36 substantially around the absorbent core 38 may comprise either intermittent bonds or, preferably, a continuous autogenous bond. The perimeter bond 40 may be undulatory along the intermediate portion of the core 38, imparting a scalloped edge and greater flexibility therein.

Significantly, the absorbent structure 32 may be integrated into the outer cover 12 in the waist attachment zones 52, 54 while the outer cover is stretched in the cross-body direction 41. Preferably, the longitudinal length of the free-span zone 56 in the front 28 and rear 30 panels is at least about 2.5 inches or the longitudinal length of the side seams 27.

A preferred method of integrating the absorbent insert structure 32 into the resiliently stretchable breathable outer cover 12 and assembling the instant disposable absorbent undergarment comprises the steps of providing the outer cover with opposed front 13 and rear 14 waist sections, a central crotch section 16, front 28 and rear 30 panels between the crotch and the waist sections prestretching the outer cover more than about 20% in a cross-body direction 41 parallel to the waist sections while superposing the insert 32 upon an inner surface of the outer cover, then bonding the longitudinally opposed ends 62, 64 of the insert to the waist sections in the selected waist attachment zones 52, 54, defining one or more free-span zones 56 allowing substantially unrestricted functional stretchability of the outer cover 12 underlying the free-span zones 56. One aspect of the present integration method comprises the step of inwardly folding over the outermost edges of the waist sections 13, 14 forming waist hems 66 entrapping the longitudinally opposed ends 62, 64 of the absorbent insert therein and bonding the opposed ends 62, 64 of the insert within the waist hems 66 at the waist attachment zones 52, 54. As disclosed above, however, the waist opening may be elasticized by a breathable elastomeric nonwoven laminar border strip rather than elasticized waist hems. Finally, the side panels 27 are closed and joined together at the side seams 42 by the ultrasonic or thermal bonds 46. In use, the garment 10 is slipped on the body in the same way as a reusable cloth underpant and may be slipped down over the hips by the wearer when using the toilet. Should the garment become soiled, the side seams 27 may be manually separated by tearing away the bonds 46, then removing the garment 10 from the wearer.

With respect to the physical properties required of the separable side seams 42 fastening system, it has been found that the autogenous bonds 46 should provide the seams 42 with a peel strength of from about 600 grams to about 2,500 grams depending upon the outer cover material and the ability or strength of the user, e.g., a parent, to tear open the side seams 42. The side seam 42 should have a shear strength greater than about 3,750 grams per square inch. The instant invention, during wear, maintains the dimensional integrity of the garments with minimal sagging of the waist or gapping and blousing at the hips.

Figure 2:
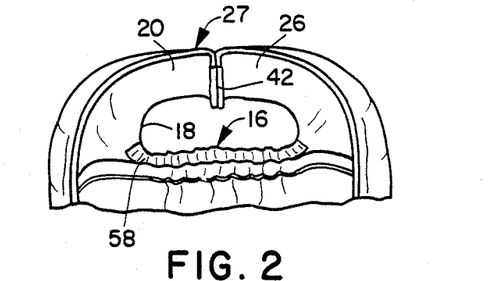
FIG. 2 is a partial internal perspective view of the invention.
Figure 3:
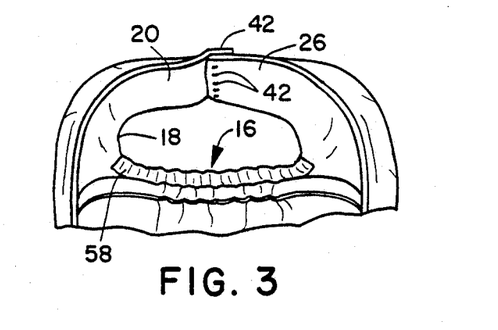
FIG. 3 is a partial internal perspective view of the invention.
Figure 4:
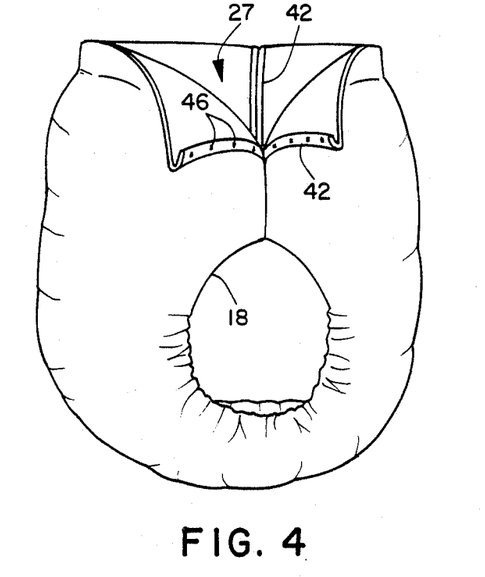
FIG. 4 is an external sequential view of FIG. 2.
Figure 5:
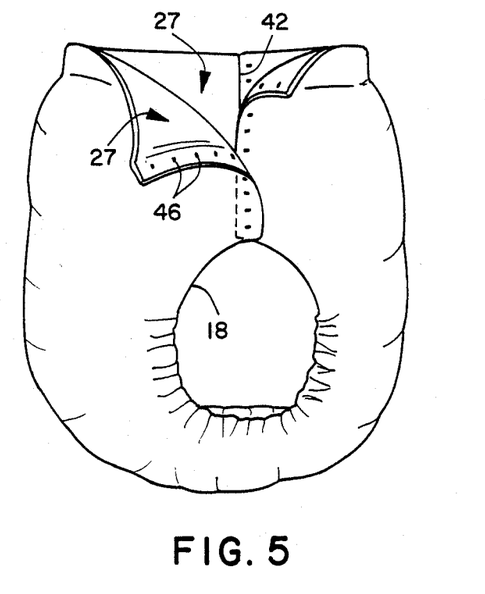
FIG. 5 is an external sequential view of FIG. 3.

FIGS. 1-3 show various configurations of the side seam 42 which may be outwardly facing (FIG. 1), inwardly facing (FIG. 2) or overlapping (FIG. 3). The side seam 42 is shown in FIGS. 4 and 5 as the seam 42 would be manually separated, in the case of the internally facing side seam (FIG. 4) and the overlapping seam (FIG. 5). Alternatively, the side seam 42 could comprise perforations (not shown) in the side panels 27.

FIGS. 8-11 show a disposable diaper 10 of the instant invention as it would be worn by a baby wherein the disposable diaper has a neat, trim fit and appearance when viewed from different perspectives.

Figure 11:
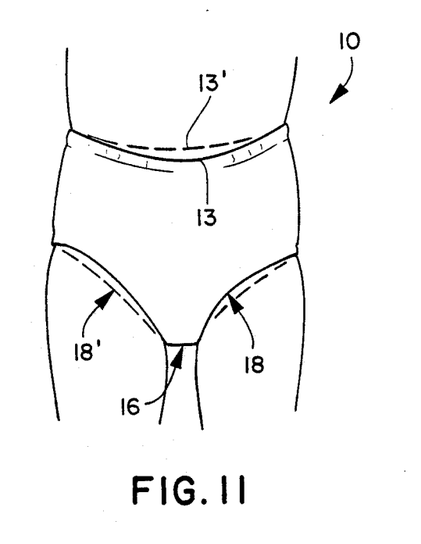
FIG. 11 is a front view of the disposable absorbent undergarment of the present invention showing the disposition of the garment on the baby after being worn for a period of time.

FIG. 11 illustrates the dimensional integrity of the diaper, as shown by the minimal extent the diaper moves or sags from an initial position as indicated by the dashed lines 18' and 13' after being worn by an infant for a period of time.

Turning now to the outer cover 12 of the present invention, which is preferably made from a resiliently stretchable elastomeric nonwoven laminar material having a stretchability of from about 20 percent to about 200 percent. The term stretchability as used herein is defined by the following relationship:

stretchability =

((final dimension − initial dimension)/initial dimension) × 100%

Since the outer cover 20 is also resilient, the outer cover returns essentially to its initial dimension when the stretching force is removed.

One such resiliently stretchable material is disclosed in U.S. patent application, Ser. No. 760,698 in the name of Tony J. Wisneski and Michael T. Morman, assigned to the assignee of the present application, entitled "Polyolefin-containing Extrudable Compositions and Methods for their Formation into Elastomeric Products", the disclosure of which is incorporated herein by reference and relied upon. That application provides extrudable elastomeric compositions which, after extrusion, solidify to form elastomeric products such as, for example, fibrous nonwoven elastomeric webs. The extrudable elastomeric compositions are blends of (1) from at least about 10 percent, by weight, of an A-B-A' block copolymer, where "A" and "A'" are each a thermoplastic polymer endblock which includes a styrenic moiety such as a poly(vinyl arene) and where "B" is an elastomeric poly(ethylene-butylene) midblock, with (2) from greater than 0 percent, by weight, to about 90 percent, by weight, of a polyolefin which, when blended with the A-B-A' block copolymer and subjected to appropriate elevated pressure and elevated temperature conditions, is extrudable, in blended form, with the A-B-A' block copolymer. The A-B-A' block copolymer serves to impart elastomeric properties to products formed from the extrudable composition and the presence of the polyolefin in the blend serves to reduce the viscosity of the composition as compared to the viscosity of the neat, that is, pure, A-B-A' block copolymer and thus enhances the extrudability of the composition.

Preferably, the "A" and "A'" thermoplastic styrenic moiety containing endblocks of the block copolymer are selected from the group including polystyrene and polystyrene homologs such as, for example, poly(alpha-methylstyrene). In some embodiments the "A" and "A'" thermoplastic styrenic moiety containing endblocks are identical. Preferably, the polyolefin is selected from the group including at least one polymer selected from the group including polyethylene, polypropylene, polybutene, ethylene copolymers, propylene copolymers, butene copolymers or blends of two or more of these materials.

The blend usually includes from at least about 20 percent, by weight, to about 95 percent, by weight, of the block copolymer and from at least about 5 percent, by weight, to about 80 percent, by weight, of the polyolefin. For example, the blend may include from about 30 percent, by weight, to about 90 percent, by weight, of the block copolymer and from about 10 percent, by weight, to about 70 percent, by weight, of the polyolefin. Preferably, the blend includes from about 50 percent, by weight, to about 90 percent, by weight, of the block copolymer and from about 10 percent, by weight, to about 50 percent, by weight, of the polyolefin. For example, the blend may include from about 50 percent, by weight, to about 70 percent, by weight, of the block copolymer and from about 30 percent, by weight, to about 50 percent, by weight, of the polyolefin. One blend includes about 60 percent, by weight, of the polyolefin.

The extrudable composition is extruded or otherwise formed, such as, for example, by molding, for example, injection molding, at an appropriate, that is effective, combination of elevated pressure and elevated temperature conditions. These conditions will vary depending on the polyolefin utilized. For example, the extrudable composition should be extruded or otherwise formed at a temperature of at least about 125 degrees Centigrade if polyethylene is utilized as the polyolefin in the blend or at least about 175 degrees Centigrade if polypropylene is utilized in the blend, for example, at a temperature of from at least about 290 degrees Centigrade to about 345 degrees Centigrade, more specifically, at a temperature of from at least about 300 degrees Centigrade to about 335 degrees Centigrade, into elastomeric products such as, for example, elastomeric fibers, which may be collected as a fibrous nonwoven elastomeric web.

Preferably the blends are extrudable within the above-defined temperature ranges at elevated pressures within the die tip, (for example, within the extrusion capillaries of a die tip having thirty (30) extrusion capillaries per lineal inch of die tip with each of the capillaries having a diameter of 0.0145 inches and a length of 0.113 inches) of no more than about 300 pounds per square inch, gage, for example, from pressures of from about 20 pounds per square inch, gage, to about 250 pounds per square inch, gage. More specifically, the blends are extrudable within the above-defined temperature ranges at pressures of from about 50 pounds per square inch, gage, to about 250 pounds per square inch, gage, for example, from about 125 pounds per square inch, gage, to about 225 pounds per square inch, gage. Higher elevated pressures can be utilized with other die designs having a lower number of capillaries per inch of die, but, generally speaking, lower production rates result.

Importantly, it has been found that the extrudable compositions are extrudable at satisfactory throughput rates because the presence of the polyolefin in the extrudable composition reduces the viscosity of the extrudable composition, as compared to the viscosity of the neat, that is, pure, block copolymer, to satisfactory levels. This reduced viscosity proportionally reduces the die tip pressure if all other parameters remain the same. For example, the viscosity of the extrudable compositions will generally be less than about 500 poise when extruded at the above-defined elevated temperature and elevated pressure ranges. Preferably, the viscosity of the extrudable composition is less than about 300 poise when extruded at the above-defined elevated temperatures and elevated pressure ranges. For example, the viscosity of the extrudable composition may be from at least about 100 poise to about 200 poise when extruded at the above-identified elevated temperature pressure conditions.

Because the polyolefin reduces the viscosity of the blend, as compared to the viscosity of the block copolymer, the extrudable composition is extrudable within the above-identified elevated temperature and elevated pressure ranges, through a die tip having, for example, thirty capillaries per inch of die tip with the capillaries having a diameter of about 0.0145 inches and a length of about 0.113 inches at a rate of from at least about 0.02 grams per capillary per minute to about 1.7 or more grams per capillary per minute. For example, the extrudable composition may be extruded through the above-identified die tip having capillaries with a diameter of about 0.0145 inches and a length of about 0.113 inches at the rate of from at least about 0.1 grams per capillary per minute to about 1.25 grams per capillary per minute. Preferably, the extrudable composition is extrudable through the above-identified die tip having capillaries with a diameter of about 0.0145 inches and a length of about 0.113 inches at the rate of from at least about 0.3 grams per capillary per minute to about 1.1 grams per capillary per minute.

The extrudable composition may be formed into fibrous nonwoven elastomeric webs preferably having microfibers with an average diameter of not greater than about 100 microns, and preferably having an average basis weight of not more than about 300 grams per square meter, for example, an average basis weight of from about 5 grams per square meter to about 100 grams or more per square meter. More specifically, an average basis weight of from about 10 grams per square meter to about 75 grams per square meter. For example, a fibrous nonwoven elastomeric web may be formed by extruding the extrudable composition at an appropriate, that is, effective, combination of elevated temperature and elevated pressure conditions. Preferably, the extrudable composition is extruded at a temperature of from at least about 125 degrees Centigrade if the polyolefin is polyethylene or at least about 175 degrees Centigrade if the polyolefin is polypropylene, for example, from about 290 degrees Centigrade to about 345 degrees Centigrade, more specifically from about 300 degrees Centigrade to about 335 degrees Centigrade. Preferably, the extrudable composition is extruded within the above-identified temperature ranges and pressures, within the die tip, (for example, within the extrusion capillaries of a die tip having thirty (30) extrusion capillaries per lineal inch of die tip with each of the capillaries having a diameter of about 0.0145 inches and a length of 0.113 inches) of no more than about 300 pounds per square inch, gage, for example, from about 20 pounds per square inch, gage, to about 250 pounds per square inch, gage. More specifically, the extrudable composition is extruded at a pressure within the capillaries of the above-identified die tip of from about 50 pounds per square inch, gage, to about 250 pounds per square inch, gage, for example, from about 125 pounds per square inch, gage, to about 225 pounds per square inch, gage.

In the formation of elastomeric nonwoven webs, the extrudable composition is extruded, at the above-defined elevated temperature and elevated pressure conditions at a rate of from at least about 0.02 gram per capillary per minute to about 1.7 or more grams per capillary per minute, for example, from at least about 0.1 gram per capillary per minute to about 1.25 grams per capillary per minute, more specifically, from at least about 0.3 gram per capillary per minute to about 1.1 grams per capillary per minute, through a die having a plurality of small diameter extrusion capillaries, as molten threads into a gas stream which attenuates the molten threads to provide a gas-borne stream of microfibers which are then formed into the fibrous nonwoven elastomeric web upon their deposition on a collecting arrangement. The attenuating gas stream is applied to the molten threads at a temperature of from at least about 100 degrees Centigrade to about 400 degrees Centigrade, for example, from about 200 degrees Centigrade to about 350 degrees Centigrade and at a pressure of from at least about 0.5 pound per square inch, gage, to about 20 pounds per square inch, gage, for example, from at least about 1 pound per square inch, gage, to about 10 pounds per square inch, gage. The thread attenuating gas stream may be an inert, non-oxidizing, gas stream such as, for example, a stream of nitrogen gas. In some embodiments the velocity and temperature of the thread-attenuating gas stream is adjusted so that the fibers are collected as substantially continuous fibers having diameters of from about ten (10) microns to about sixty (60) microns, for example, from at least about ten (10) microns to about forty (40) microns. The fibrous nonwoven elastomeric webs so formed will include elastomeric fibers composed of from at least about 10 percent, by weight, of the block copolymer and greater than 0 percent, by weight, and up to about 90 percent, by weight, of the polyolefin. The fibers are usually composed from at least about 20 percent, by weight, to about 95 percent, by weight, of the block copolymer and from at least about 5 percent, by weight, to about 80 percent, by weight of the polyolefin. For example, the fibers may be composed from at least about 30 percent, by weight, to about 90 percent, by weight, of the block copolymer and from at least about 10 percent, by weight, to about 70 percent, by weight, of the polyolefin. Preferably, the fibers are composed from about 50 percent, by weight, to about 90 percent, by weight, of the block copolymer and from at least about 10 percent, by weight, to about 50 percent, by weight, of the polyolefin. For example, the fibers may be composed from at least about 50 percent, by weight, to about 70 percent, by weight, of the block copolymer and from at least about 30 percent, by weight, to about 50 percent, by weight, of the polyolefin.

Another such resiliently stretchable material is disclosed in U.S. patent application, Ser. No. 760,437 in the name of Jack D. Taylor and Michael J. Vander Wielen and assigned to the assignee of the present application, entitled "Composite Elastomeric Material and Process for Making the Same", the disclosure of which is incorporated herein by reference and relied upon. That application provides a method of producing a composite elastic material comprising at least one gatherable web bonded to at least one elastic web, the method comprising (a) tensioning an elastic web (which may comprise a fibrous web such as a nonwoven web of elastomeric fibers, for example, meltblown elastomeric fibers) to elongate it; (b) bonding the elongated elastic web to at least one gatherable web under conditions which soften at least portions of the elastic web to form a bonded composite web; and (c) relaxing the composite web immediately after the bonding step whereby the gatherable web is gathered to form the composite elastic material. The fibrous elastic web can also be maintained in a stretched condition during the bonding, at an elongation of at least about 25 percent, preferably about 25 percent to over 500 percent, for example, about 25 percent to 550 percent elongation during the bonding. The method also includes bonding the elongated elastic web to the gatherable web by overlaying the elastic and gatherable webs and applying heat and pressure to the overlaid webs, for example, by heating bonding sites on the elastic web to a temperature of from at least about 65 degrees Centigrade to about 120 degrees Centigrade, preferably from at least about 70 degrees Centigrade to about 90 degrees Centigrade.

That application also provides an elastic composite material comprising an elastic web bonded to at least one gatherable web which is extensible and contractible with the elastic web upon stretching and relaxing of the composite material, the elastic composite material being made by a method as described above. Also provided is an elastic web that is bonded to the gatherable web at a plurality of spaced-apart locations in a repeating pattern and the gatherable web is gathered between the bonded locations. The elastic web may comprise a nonwoven web of elastomeric fibers, preferably elastomeric microfibers, such as, for example, an elastomeric nonwoven web of meltblown elastomeric fibers or an elastomeric film.

The elastic composite material may include one or more of the following in any combination: the elastomeric fibers, preferably meltblown elastomeric fibers, may be formed from material selected from the group including (i) A-B-A' block copolymers wherein "A" and "A'" may be the same or different endblocks and each is a thermoplastic polymer endblock or segment which contains a styrenic moiety such as polystyrene or polystyrene homologs, and "B" is an elastomeric polymer midblock or segment, for example, a midblock selected from the group including poly(ethylene-butylene), polyisoprene and polybutadiene, with poly(ethylene-butylene) being preferred and (ii) blends of one or more polyolefins with the A-B-A' block copolymers of (i) where "B" is a poly(ethylene-butylene) midblock; each of the "A" and "A'" endblocks may be selected from the group consisting of polystyrene and polystyrene homologs, for example, poly(alpha methylstyrene), and where the elastomeric fibers are formed from a blend of one or more polyolefins with an A-B-A' block copolymer where "B" is a poly(ethylene-butylene) midblock, the polyolefin is selected from one or more of polyethylene, polypropylene, polybutene, ethylene copolymers, propylene copolymers and butene copolymers; the elastomeric film and the elastomeric fibers which form the elastomeric nonwoven web, for example, the meltblown microfibers, are composed of at least 10 percent, for example at least 20 percent, more specifically at least 30 percent, for example, from about 10 percent to 90 percent, by weight, of the aforesaid A-B-A' block copolymers and greater than 0 percent, by weight, for example, from about 90 percent to about 10 percent, by weight, of the polyolefin; the elastic web, for example, a fibrous elastic web, is bonded to the gatherable web at a plurality of spaced-apart locations in a repeating pattern and the gatherable web is gathered between the bonded locations; the elastic web preferably has a low basis weight of from about 5 to about 300, preferably from about 5 to about 200, grams per square meter, for example, from about 5 to about 100 grams per square meter, although its basis weight can be much higher; the gatherable web is a nonwoven, non-elastic material, preferably one composed of fibers formed from materials selected from the group including polyester fibers, for example, poly(ethylene terephthalate) fibers, polyolefin fibers, polyamide fibers, for example, nylon fibers, cellulosic fibers, for example, cotton fibers, and mixtures thereof. Alternatively, the gatherable web may be any suitable woven fabric. In a particular aspect, the composition of the A-B-A' polymer used is such that the sum of the molecular weight of "A" with the molecular weight of "A'" is from about 14 to 31 percent (from about 14 to 29 percent when "B" is poly(ethylene-butylene)) of the molecular weight of the A-B-A' block copolymer.

A further such resiliently stretchable material is disclosed in U.S. patent application, Ser. No. 760,449, in the name of Michael J. Morman, and assigned to the assignee of the present invention, entitled "Composite Nonwoven Elastic Web", the disclosure of which is incorporated herein by reference. That application is directed to a process for producing a composite nonwoven elastic web which is composed of a nonwoven elastic web that is joined to a fibrous nonwoven gathered web. In particular, the process disclosed therein produces a composite nonwoven elastic web which, in its relaxed, nonstretched state, is composed of a gathered nonwoven fibrous web that is joined to a nonwoven elastic web with the nonwoven elastic web having been relaxed from a stretched, biased length to a relaxed, unbiased, nonstretched length so as to gather the fibrous nonwoven gathered web. An important feeature of the process disclosed therein is that the fibrous nonwoven gatherable web is formed directly onto a surface of the nonwoven elastic web while the nonwoven elastic web is maintained in a stretched, biased and elongated condition. The nonwoven elastic web may be formed by, for example, a meltblowing process or any other process for forming a nonwoven elastic web. For example, the nonwoven elastic web could be an apertured web of an elastic film as opposed to a meltblown fibrous nonwoven elastic web. The formed nonwoven elastic web has a normal relaxed, nonstretched, nonbiased length. Thereafter, the nonwoven elastic web is elongated by being stretched to a stretched, biased length. In a subsequent step of the process a fibrous nonwoven gatherable web may be formed, for example, by either a meltblowing or spunbonding process or any other process for forming a fibrous nonwoven gatherable web, directly upon a surface of the nonwoven elastic web while the nonwoven elastic web is maintained at its elongated, stretched and biased length. During formation of the fibrous nonwoven gatherable web the nonwoven elastic web is maintained at a stretched length which is at least about 125 percent, that is, at least about one and one quarter of the relaxed, unbiased length of the nonwoven elastic web. For example, the stretched, biased length of the nonwoven elastic web may be maintained in the range of from at least about 125 percent of the relaxed, unbiased length of the nonwoven elastic web to about 700 or more percent of the relaxed, unbiased length of the nonwoven elastic web. The fibrous nonwoven gatherable web is joined to the nonwoven elastic web while the nonwoven elastic web is maintained at its elongated stretched, biased length. This results in the formation of a composite nonwoven elastic web which includes the nonwoven elastic web which is joined to the fibrous nonwoven gatherable web. Because the fibrous nonwoven gatherable web is formed directly onto the surface of the nonwoven elastic web while the nonwoven elastic web is being maintained at its stretched, biased length, the nonwoven elastic web is, at this stage in the process, elongated, stretched and biased and the fibrous nonwoven gatherable web is in an ungathered but gatherable condition. In one aspect, the joining of the fibrous nonwoven gatherable web to the nonwoven elastic web is achieved by heat-bonding to fuse the two webs to each other. The heat-bonding may be carried out within the temperature range of from about 50 degrees centigrade below the melt temperature of at least one of the materials utilized to form at least one of the two webs to about the melt temperature of at least one of the materials utilized to form at least one of the two webs. At high through-put rates the heat-bonding can be carried out above the melt temperature of one or more of the materials utilized to form the webs. The heat-bonding may also be carried out under appropriate conventional pressurized conditions. If desired, conventional sonic bonding techniques may be substituted for the heat-bonding steps.

The application also discloses another embodiment whereby the joining of the fibrous nonwoven gatherable web to the stretched nonwoven elastic web is achieved solely by the entanglement of the individual fibers of the fibrous nonwoven gatherable web with the nonwoven elastic web during formation of the fibrous gatherable web on the surface of the elastic web. If the nonwoven elastic web is a fibrous nonwoven elastic web formed by, for example, meltblowing, entanglement of the individual fibers of the fibrous nonwoven gatherable web with the fibrous nonwoven elastic web is achieved by entanglement of the individual fibers of the fibrous gatherable web with the individual fibers of the fibrous elastic web. If the nonwoven elastic web is an apertured film, joining of the fibrous nonwoven web with the film is achieved by entanglement of the individual fibers of the fibrous gatherable web within the apertures of the film. The joining of the two webs to each other can also be achieved by forming the nonwoven elastic web out of a tacky elastic material, a process that will be discussed hereinafter. In addition, the joining of the two webs to each other may be further enhanced by applying pressure to the two webs after the gatherable web has been formed on the surface of the elastic web. Further improvement in the joining of the two webs can be obtained by applying an adhesive material to the upper surface of the nonwoven elastic web prior to formation of the fibrous nonwoven gatherable web thereon.

After joining of the two webs to each other has been achieved to form a composite elastic web, the biasing force is removed from the composite nonwoven elastic web and the composite elastic web is allowed to relax to its normal relaxed, unbiased length. Because the fibrous nonwoven gatherable web is joined to the nonwoven elastic web while the nonwoven elastic web is stretched, relaxation of the composite nonwoven elastic web results in the gatherable web being carried with the contracting nonwoven elastic web and thus being gathered. After gathering of the fibrous nonwoven gatherable web has occurred by reducing the biasing force on the composite nonwoven elastic web, the composite nonwoven elastic web may be rolled up in rolls for storage and shipment of directed to a manufacturing process for the production of products such as the disposable garments taught by the present application.

As indicated above, the process disclosed in U.S. patent application Ser. No. 760,449 can be enhanced by the utilization of a tacky fibrous nonwoven elastic web which can be formed by, for example, meltblowing microfibers of a tacky elastic material such as, for example, an A-B-A' block copolymer or blends of such A-B-A' block copolymers with poly(alpha-methylstyrene) where "A" and "A'" are each thermoplastic polystyrene or polystyrene homolog endblocks and "B" is an elastic polyisoprene midblock. In some embodiments "A" may be the same thermoplastic polystyrene or polystyrene homolog endblock as "A'". The tacky fibrous nonwoven elastic web is then elongated by being stretched to an elongated, stretched length and a fibrous nonwoven gatherable web is formed, for example, by meltblowing or spunbonding the fibrous nonwoven gatherable web, directly upon a surface of the tacky fibrous nonwoven elastic web while maintaining the fibrous nonwoven elastic web at its stretched length. As a result of the fact that the fibrous nonwoven elastic web is tacky, the fibrous nonwoven gatherable web is simultaneously formed upon and adhesively joined to the surface of the tacky fibrous nonwoven elastic web. This results in the formation of a composite nonwoven elastic web having an ungathered fibrous gatherable web adhesively joined to the tacky fibrous nonwoven elastic web with the joining of the two webs to each other being achieved by the adhesive joining which occurs during formation of the fibrous nonwoven gatherable web on the surface of the fibrous nonwoven elastic web. The adhesive joining of the two webs to each other may be increased upon application of pressure to the composite nonwoven elastic web by passing the composite nonwoven elastic web through the nip between rollers, which may be unheated, after the composite web has been formed but before the fibrous tacky nonwoven elastic web is allowed to relax. The adhesive joining may be further enhanced by application of an adhesive material to the surface of the tacky fibrous nonwoven elastic web prior to formation of the gatherable web thereon. The composite nonwoven elastic web is then allowed to relax to its normal relaxed, unbiased length. Because the fibrous nonwoven gatherable web is joined to the tacky fibrous nonwoven elastic web while the tacky fibrous nonwoven elastic web is in a stretched condition, relaxation of the composite nonwoven elastic web and thus the tacky fibrous nonwoven elastic web results in the gatherable web being carried with the contracting fibrous nonwoven elastic web and thus being gathered. After gathering of the fibrous nonwoven gatherable web has occurred the composite nonwoven elastic web may be rolled up in rolls for storage or directly applied to a manufacturing process for the production of disposable garments such as the disposable garments taught by the present application.

The U.S. patent application, Ser. No. 760,449 is also directed to a composite nonwoven elastic web composed of a nonwoven elastic web that is joined to a gatherable fibrous nonwoven web which has been gathered and with the composite web having been formed by any of the embodiments of the process disclosed above. In particular, the composite nonwoven elastic web, in its relaxed, nonstretched state, is composed of a nonwoven elastic web that is joined to a fibrous nonwoven gathered web which has been gathered as a result of the nonwoven elastic web having been relaxed from an elongated stretched, biased length to a relaxed, unbiased nonstretched length. Exemplary elastomeric materials for use in formation of the fibrous nonwoven elastic web include polyester elastomeric materials, polyurethane elastomeric materials, and polyamide elastomeric materials. Other elastomeric materials for use in formation of the fibrous nonwoven elastic web include (a) A-B-A' block copolymers, where "A" and "A'" are each a thermoplastic polymer endblock which includes a styrenic moiety and where "A" may be the same thermoplastic polymer endblock as "A'", such as a poly(vinyl arene), and where "B" is an elastomeric polymer midblock such as a conjugated diene or a lower alkene or (b) blends of one or more polyolefins or poly(alpha-methyl styrene) with A-B-A' block copolymers, where "A" and "A'" are each a thermoplastic polymer endblock which includes a styrenic moiety, where "A" may be the same thermoplastic polymer endblock as "A'", such as a poly(vinyl arene) and where "B" is an elastomeric polymer midblock such as a conjugated diene or a lower alkene. The "A" and "A'" endblocks may be selected from the group including polystyrene and polystyrene homologs and the "B" midblock may be selected from the group including polyisoprene, polybutadiene or poly(ethylene-butylene). If "A" and "A'" are selected from the group including polystyrene or polystyrene homologs and "B" is poly(ethylene-butylene), materials which may be blended with these block copolymers are polymers, including copolymers of ethylene, propylene, butene, other lower alkenes or one or more of these materials. If "A" and "A'" are selected from the group including polystyrene or polystyrene homologs and "B" is a polyisoprene midblock, a material for blending with this type of block copolymer is poly(alpha-methylstyrene).

As used in the U.S. patent application Ser. No. 760,449, and as contemplated herein, the term "nonwoven web" or "nonwoven layer" includes any web of material which has been formed without use of textile weaving processes which produce a structure of individual fibers which are interwoven in an identifiable repeating manner. Specific examples of nonwoven webs would include, without limitation, a meltblown nonwoven web, a spunbonded nonwoven web, an apertured film, a microporous web, elastomeric netting or a carded web of staple fibers.

It is to be clearly understood that the descriptions of methods for making a material suitable for outer cover 12 and the description of materials suitable for the outer cover 12 are exemplary only and not meant to be limiting.

The bodyside liner 34 may be airlaid, a bonded carded web, a powder-bonded carded web or a pattern bonded, spunbonded web of synthetic fibers such as polypropylene, polyester and the like.

Various materials are contemplated for use as the absorbent core 38, including fibrous materials, foams, particulates, etc. In general, the most economical liquid aborbent material for use in disposable diapers has been an absorbent fiber. The absorbent fiber most commonly used is cellulosic fiber such as comminuted wood pulp, commonly known in the art as "pulp fluff," or simply "fluff."

Comminuted wood pulp (fluff) is preferred as an absorbent fiber, but other cellulose fibers such as cotton linters can be used. The preferred fluff is southern pine kraft wood pulp (i.e., made according to the sulfate process commonly known in the art) which has been bleached, such as can be purchased from International Paper Company. Other softwood fluffs may be purchased from Kimberly-Clark Corporation, such as CR-54. Various hardwood fluffs may also be blended with the softwood fluffs to form the absorbent composite. A water-swellable hydrogel material, preferably in particulate form, may be used in a number of various arrangements within the absorbent composite in order to decrease the bulkiness and enhance the capacity of the composite 38. It should be understood that additional elements could be provided in conjunction with those already set forth, without departing from the contemplated scope of the present invention and the description herein is not intended to be in any way limiting.

We claim:

1. An anatomically form-fitting, generally self-adjusting three dimensional disposable absorbent undergarment comprising:
   a breathable elastomeric nonwoven outer cover wherein an elastic nonwoven web is joined to one or more gatherable nonwoven webs, defining a waist opening, leg openings, a central crotch section, front and rear panels separate by said crotch section, and a pair of side panels extending between and interconnecting said leg and waist openings and said front and rear panels, respectively;
   an absorbent insert structure substantially superposable upon said front and rear panels and said crotch section, including a liquid permeable bodyside liner, a liquid impermeable barrier and an absorbent composite disposed therebetween;
   attachment means for attaching and integrating said absorbent structure into said elastomeric outer cover while allowing substantially unrestricted functional stretchability thereof; and
   nonrefastenable side seams extending between and interconnecting said leg and waist openings of each of said side panels, including manually tearable stress release means for opening and separating said side seams and removing said garment from a wearer when the same becomes soiled.

2. The invention of claim 1 wherein said insert includes opposed longitudinal ends respectively attached to said front and rear waist sections in selected front and rear waist attachment zones, defining one or more free-span zones underlying said insert wherein the functional stretchability of said outer cover in said free-span zones is substantially unrestricted.

3. The invention of claim 2 wherein said outer cover comprises externally facing and body facing surfaces and wherein said side seams comprise internally projecting pairs of marginal side edges of said front and rear panels and wherein said stress-release means comprises at least one stress-release bond joining together each of said pair of side edges.

4. The invention of claim 2 wherein said outer cover comprises externally facing and body facing surfaces and wherein said side seams comprise externally projecting pairs of marginal side edges of said front and rear panels and wherein said stress-release means comprise at least one stress-release bond joining together each of said side seams.

5. The invention of claim 2 wherein said outer cover comprises externally facing and body facing surfaces and wherein said side seams comprise overlapping pairs of marginal side edges of said front and rear panels and wherein said stress-release means comprise at least one stress-release bond joining together each of said side seams.

6. The invention of claim 3, 4 or 5 further comprising a plurality of said stress-release bonds.

7. The invention of claim 6 wherein said stress-release bonds comprise autogeneous bonds generated either thermally or ultrasonically.

8. The invention of claim 2 wherein said insert is not superposed on said side panels and said side seams are defined by a longitudinally extending series of perforations.

9. The invention of claim 6 wherein said insert is attached to said outer cover while said outer cover is in a stretched condition.

10. The invention of claim 1 wherein said stress-release means comprise autogenous bonds having a peel strength from about 600–2500 grams.

11. The invention of claim 10 wherein said stress-release means have a shear strength greater than about 3,750 grams per square inch.

* * * * *